Figure 1:
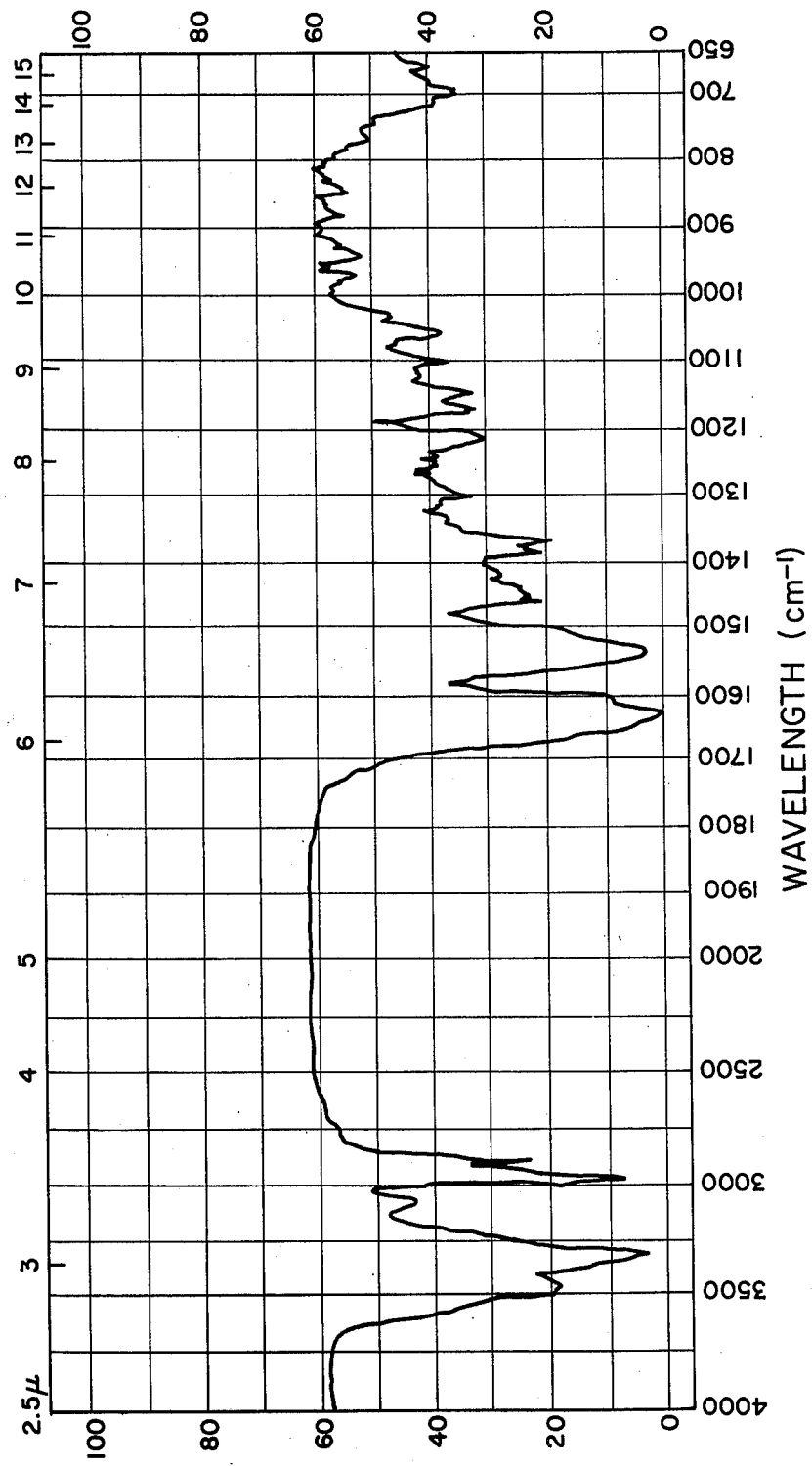

United States Patent [19]  [11] 4,091,093
Kojima et al.  [45] May 23, 1978

[54] PROTEASE INHIBITORS

[75] Inventors: Shinichi Kojima, Nishinomiya; Kazuro Nakamura, Takarazuka; Ten Koide, Toyonaka; Shigeo Ogino, Nishinomiya, all of Japan

[73] Assignee: Sumitomo Chemical Company Limited, Osaka, Japan

[21] Appl. No.: 721,503

[22] Filed: Sep. 8, 1976

[30] Foreign Application Priority Data

Sep. 12, 1975  Japan ............................. 50-111337
Sep. 16, 1975  Japan ............................. 50-112387
Sep. 16, 1975  Japan ............................. 50-112388

[51] Int. Cl.$^2$ .................... A61K 37/00; C07C 103/52
[52] U.S. Cl. .......................... 424/177; 260/112.5 R; 195/80 R; 424/116

[58] Field of Search ................. 260/112.5 R; 424/177

[56] References Cited

U.S. PATENT DOCUMENTS

| 3,840,516 | 10/1974 | Umezawa et al. | 260/112.5 R |
| 3,869,347 | 3/1975 | Umezawa et al. | 260/112.5 R |
| 3,975,366 | 8/1976 | Umezawa et al. | 260/112.5 R |

FOREIGN PATENT DOCUMENTS

| 2,554,636 | 6/1976 | Germany | 260/112.5 R |

Primary Examiner—Delbert R. Phillips
Attorney, Agent, or Firm—Cushman, Darby & Cushman

[57] ABSTRACT

Novel procidins effective for healing or preventing ulcer are produced and accumulated in the cultured product of a novel strain *Streptomyces procidinanus*.

6 Claims, 10 Drawing Figures

PROTEASE INHIBITORS

This invention relates to a novel microorganism and accumulated products produced therefrom. More particularly, this invention relates to a novel strain belonging to Genus Streptomyces, a process for producing various procidins by use of said strain and novel procidins obtained by said process.

The present inventors have made extensive studies over cultured products by microrgranisms in search for novel protease inhibitors and have discovered the fact that a novel strain belonging to Genus Streptomyces produces and accumulates in its cultured product substances capable of inhibiting potently the activities of pepsin and several acidic proteases. As the result of various studies, the present inventors were successful in isolating the protease inhibitors thus produced as crystals.

The microorganism used in the present invention is a novel strain which was isolated from soil in Fukuzaki-cho, Hyogo prefecture, Japan, and has been denominated as *Streptomyces procidinanus*. The microorganism has been deposited in Fermentation Research Institute, Agency of Industrial Science and Technology, Chiba, Japan, under acceptance number FERM-P No. 3156. It is also deposited with American Type Culture Collection, on July 29, 1976 and has been given the number ATCC No. 31233.

In the following, bacteriological properties of the microorganism of this invention (hereinafter referred to as "strain SC-4708") are described in detail. As to the description of colors, reference is made to the "color standard" by Japan Color Institute.

BACTERIOLOGICAL PROPERTIES OF THE STRAIN SC-4708

I. Morphological characteristics

A number of slightly waved aerial mycelium are observed by microscopy to grow from well-branched basal mycelium. There is no formation of spiral and whirl. Mature spore chain has ten or more spores 1.4 to 1.8 by 0.8 to 1.0 microns in size, with smooth surface.

II. Growth on various cultural media:

(1) Sucrose-nitrate agar (cultured at 27° C): Poor growth, colorless. No aerial mycelium. No soluble pigment.

(2) Glycerol-asparagine agar (cultured at 27° C): Growth, pale yellowish. Aerial mycelium, bright gray. Soluble pigment, slightly pale yellow.

(3) Glucose-asparagine agar (cultured at 27° C): Poor growth, pale yellow. Aerial mycelium scant, white. Soluble pigment, slightly pale yellow.

(4) Glucose-Czapeck agar (cultured at 27° C): Growth, pale reddish yellow. No aerial mycelium. Pigment, slightly reddish yellow.

(5) Starch agar (cultured at 27° C): Growth, pale yellow. Aerial mycelium, white. Soluble pigment, slightly pale yellow.

(6) Nutrient agar (cultured at 27° C): Very poor growth, colorless. No aerial mycelium. No soluble pigment.

(7) Peptone-glucose agar (cultured at 27° C): Growth, dull reddish yellow. Aerial mycelium, scant and white. Soluble pigment, slightly dull reddish yellow.

(8) Malt-extract agar (cultured at 27° C): Growth, greyish yellow. Aerial mycelium, white. Soluble pigment, slightly greyish yellow.

(9) Tyrosine agar (cultured at 27° C): Growth, pale yellow. Aerial mycelium, very slightly white. No soluble pigment. Tyrosinase reaction, negative.

(10) Calcium-malate agar (cultured at 27° C): Poor growth. No aerial mycelium. No soluble pigment. Calcium-malate on circumference of the growth not dissolved.

(11) Potato slant (cultured at 27° C): No growth after 21 days.

(12) Carrot slant (cultured at 27° C): No growth after 21 days.

(13) Horse serum (cultured at 30° C): No growth after 21 days.

(14) Cellulose (cultured at 27° C): No growth after 21 days.

(15) Yeast-malt agar (cultured at 27° C): Abundant growth, yellowish pink to pale pink. Aerial mycelium, bright gray. No soluble pigment.

(16) Oatmeal gear (cultured at 27° C): No growth after 21 days.

(17) Egg (cultured at 27° C): No growth after 21 days.

(18) Milk (cultured at 37° C): No growth after 21 days.

(19) Gelatin-stab (cultured at 20° C): Growth, colorless to pale yellow. Aerial mycelium, white. No soluble pigment. No substantial gelatin liquefaction.

(20) Peptone water (cultured at 27° C): No growth after 21 days.

III. Physiological characteristics:

(1) Growth temperature range:

The results of experiments at 20° C, 24° C, 27° C, 30° C, and 37° C by use of Glucose-asparagine agar as culture media show that there is growth at each temperature except at 37° C. Optimum growth temperature seems to be from 27° to 30° C.

(2) Utilization of carbon sources (cultured on Pridham-Gottrieb agar at 27° C):

Good growth with utilization of glucose and galactose. Xylose, arabinose, rhamnose, fructose, saccharose, maltose, lactose, raffinose, inulin, mannitol, sorbitol, dulcitol, inositol and salicin are not utilized.

To summarize the above characteristics, the strain SC-4708 belongs to Genus Streptomyces; its aerial mycelium forms neither whirl nor spiral, spores being smoothly surfaced; the strain is specific in poor growth except on yeast-malt agar, especially growth at 37° C is extremely bad; in spite of such a poor growth, it has peculiar activity in hydrolyzing starch; it belongs to non-chromogenic type microorganism with growth, colorless, pale yellow or pale brown, aerial mycelium of white or bright gray being slightly formed and soluble pigment being not substantially recognized; it is negative all in gelatin liquefaction, coagulation and peptone formation of defatted milk, dissolution of calcium-malate and reduction of nitrate. When reference is made to known microorganisms having these characteristics, there is found no similar strain. But, as the strain having relatively similar characteristics, *Streptomyces omiyaensis* is found. The characteristics of the strain SC-4708 are compared with the description of this strain in the literatures (1) Bergey's "Manual of Determinative Bacteriology," 8th ed., page 762, 1974 and (2) Waksman "The Actinomycetes" vol. 2, page 254 to give the result as shown in the following Table:

|  | SC-4708 | Streptomyces omiyaensis |
|---|---|---|
| Whirl formation | − | − |
| Spiral formation | − | − |
| Spore surface | smooth | smooth |
| Color of aerial mycelium | white-bright gray | gray |
| Color of growth | colorless-pale yellow | white-pale yellow |
| Melanin pigment | − | − |
| Hydrolysis of starch | + | + |
| Proteolysis | − | + |
| Gelatin liquefaction | − | ∓ |
| Utilization of carbon sources |  |  |
| D-glucose | + | + |
| D-galactose | + | + |
| D-xylose | − | + |
| L-rhamnose | − | + |
| D-fructose | − | + |
| Metabolic products produced | Procidins | Chloramphenicol |

As apparently seen from the above Table, the strain SC-4708 resembles *Streptomyces omiyaensis* but differs therefrom in proteolysis and utilization of carbon sources and further in that it does not produce chloramphenicol. Accordingly, it is proper to conclude that the strain 4708 is a new strain and therefore it is denominated as *Streptomyces procidinanus*.

Actinomycetes in general are liable to cause mutation artificially or naturally. Hence, *Streptomyces procidinanus* of this invention is inclusive of all the mutants thereof.

The novel procidins which can be produced according to the process of this invention are represented by the general formula:

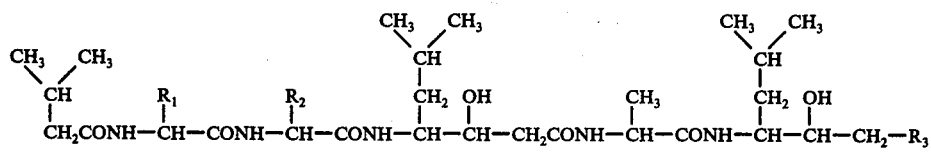

wherein $R_1$ and $R_2$, which may either be identical or different, represent isopropyl or isopropyl methyl; and $R_3$ represents hydrogen when both $R_1$ and $R_2$ are isopropyl or carboxylic when $R_1$ and $R_2$ are different or both $R_1$ and $R_2$ are isopropyl methyl, said procidin occurring as a mixture of compounds when $R_1$ and $R_2$ different.

To be more specific, the strain SC-4708 of this invention produces and accumulates the novel procidins as shown below which are useful for preventing gastric or duodenal ulcer:

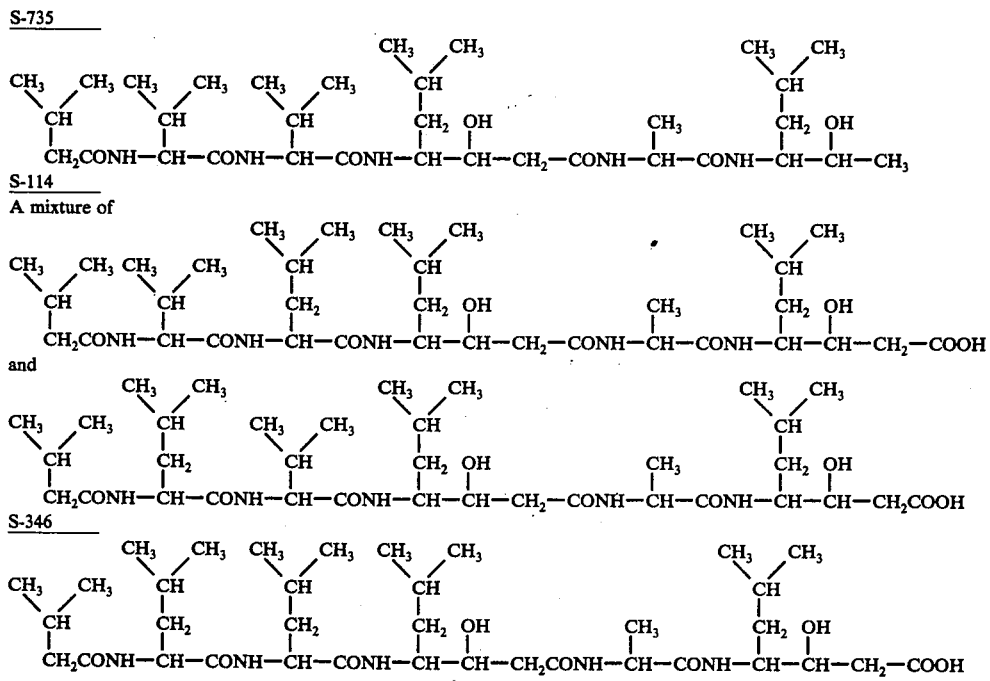

Furthermore, the strain SC-4708 produces the procidin (S-735 A) as disclosed in British Pat. No. 1,314,231, shown below, which is useful as anti-gastric or duodenal ulcer agent and its methyl ester derivative (S-735-M) in cultured product and therefore it can be used for producing these compounds.

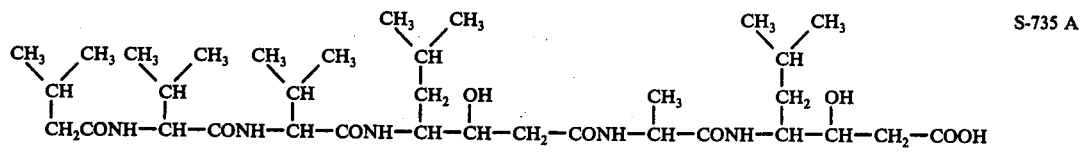

Accordingly, in its broadest aspect, the present invention provides a process for producing at least one procidins of the general formula:

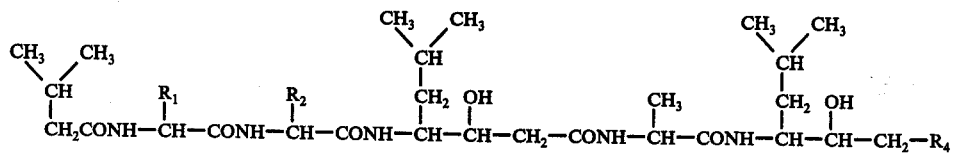

wherein $R_1$ and $R_2$, which may either be identical or different, represent isopropyl or isopropyl methyl; and $R_4$ represents hydrogen, carboxylic or methyl carboxylate when both $R_1$ and $R_2$ are isopropyl, or carboxylic when $R_1$ and $R_2$ are different or both $R_1$ and $R_2$ are isopropyl methyl, said procidin occurring as a mixture of compounds when $R_1$ and $R_2$ are different, which comprises cultivating *Streptomyces procidinanus* in an adequate medium and isolating the resulted procidin.

Figure 2:
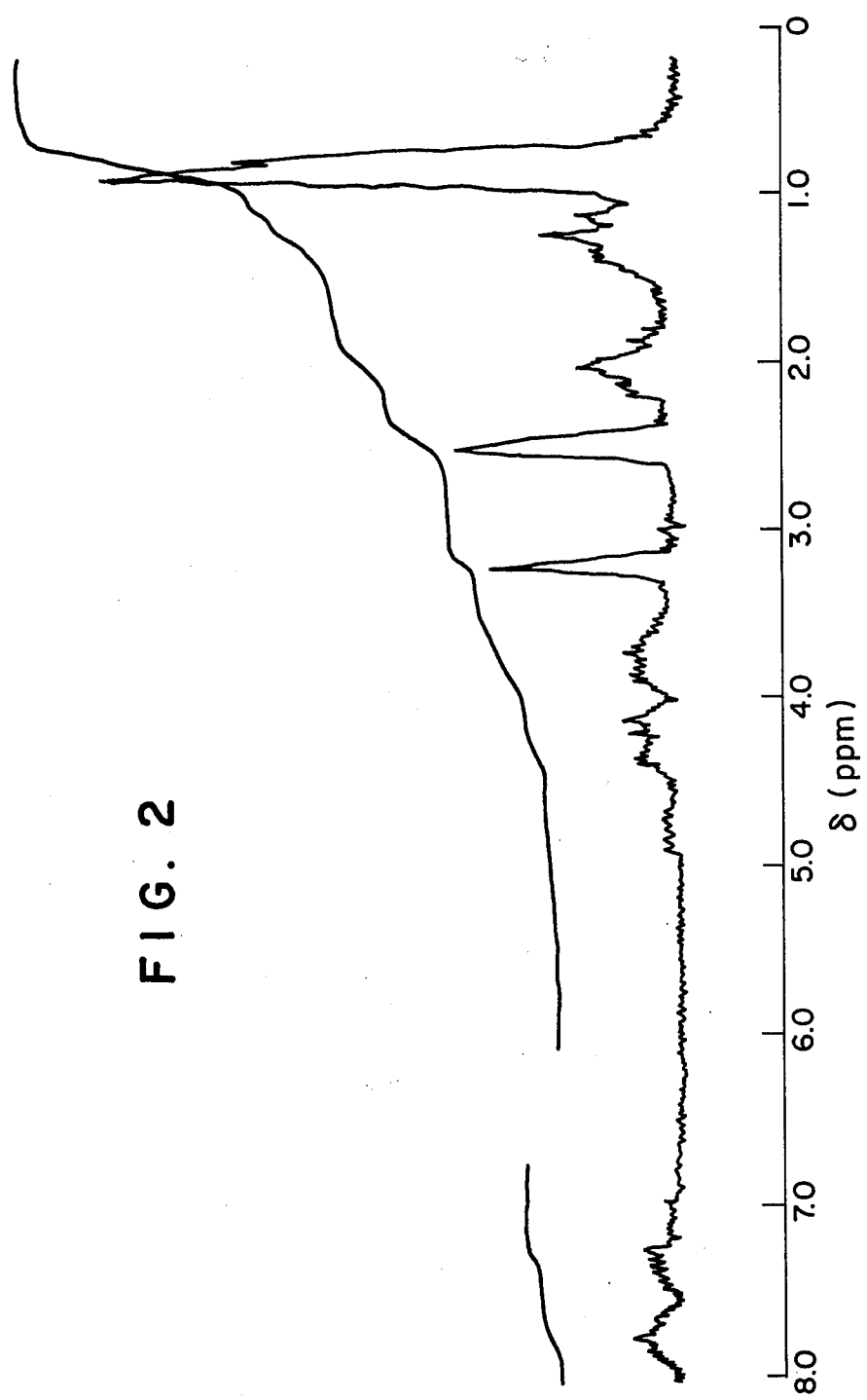
Figure 3:
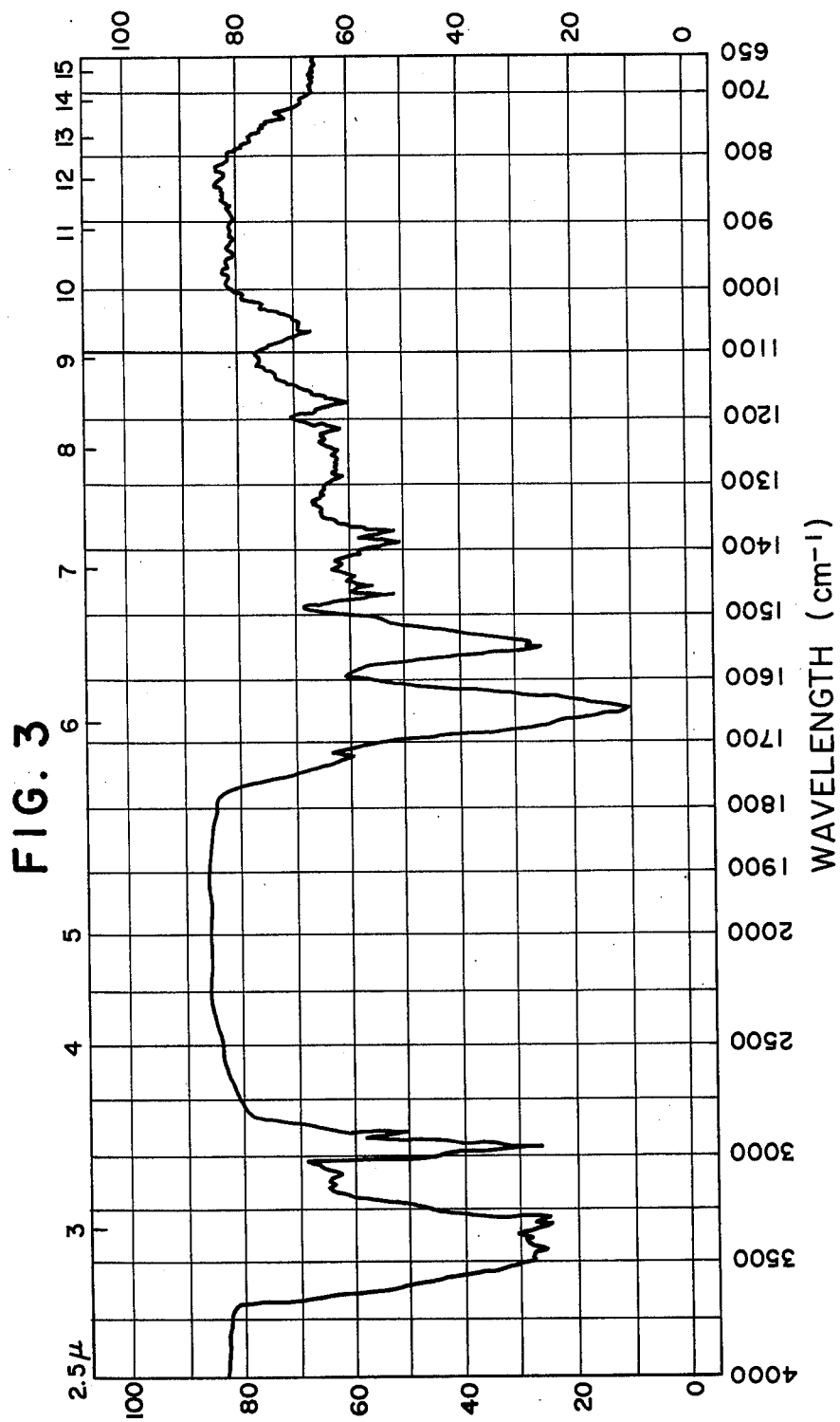
Figure 4:
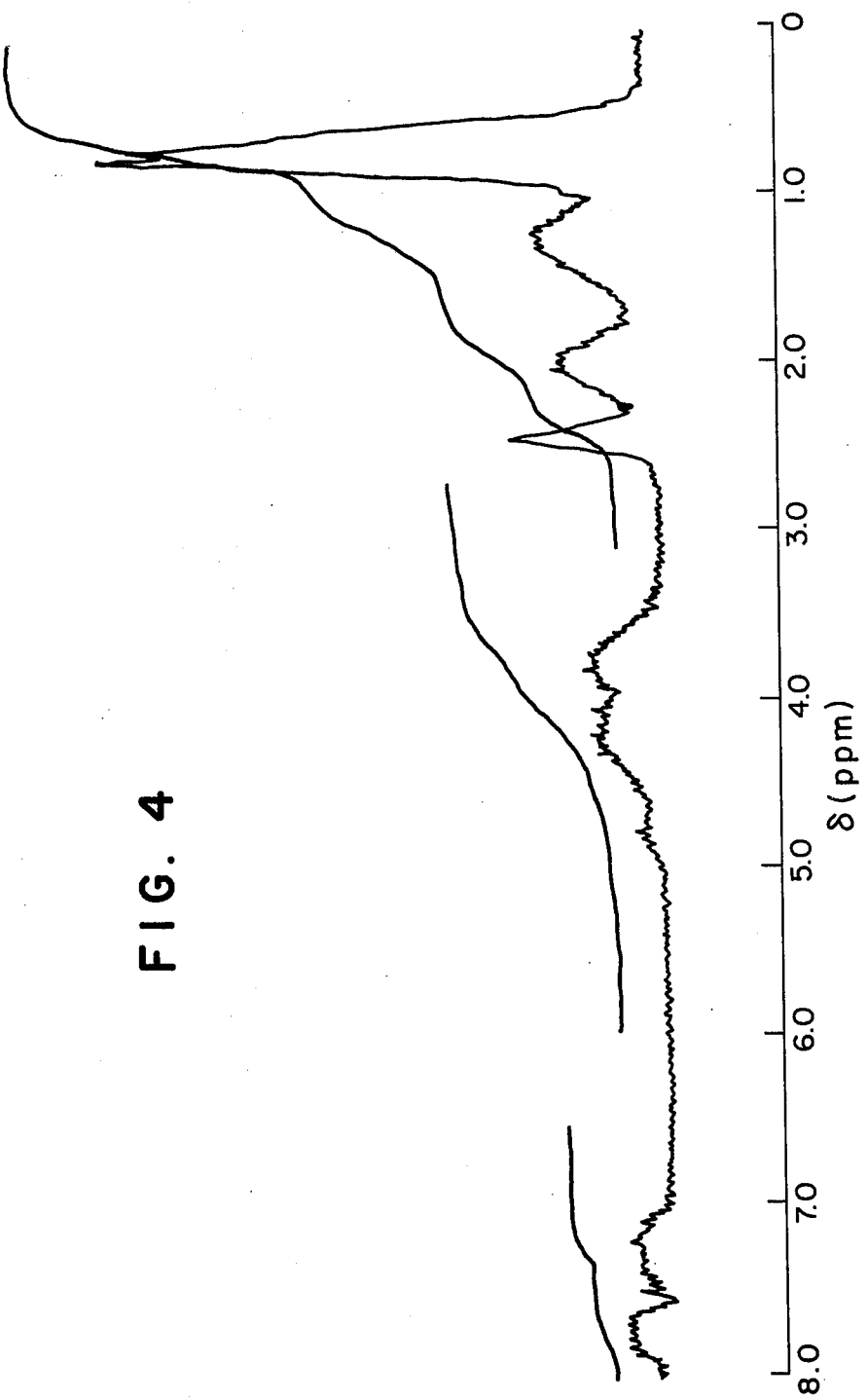
Figure 5:
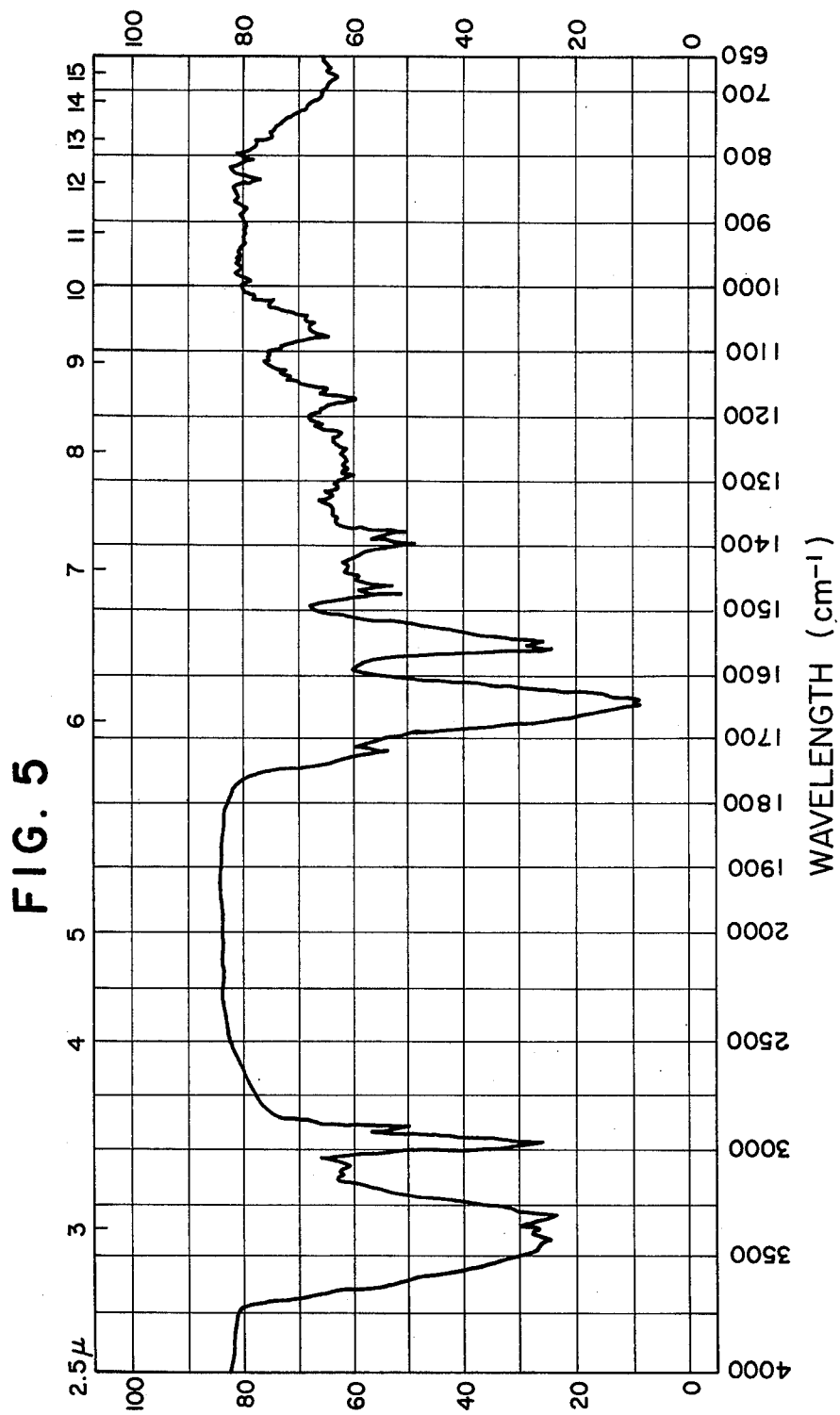
Figure 6:
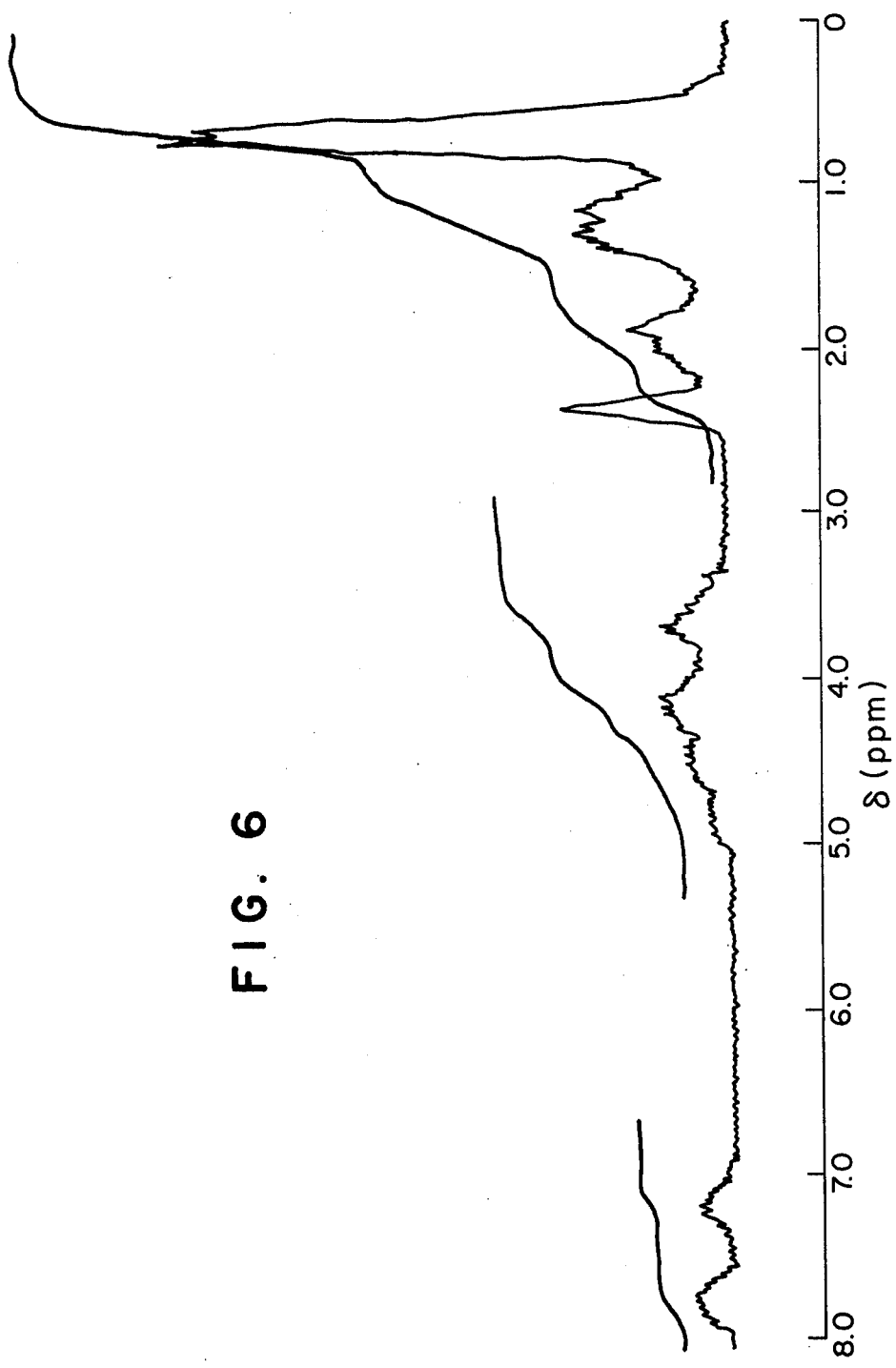
Figure 7:
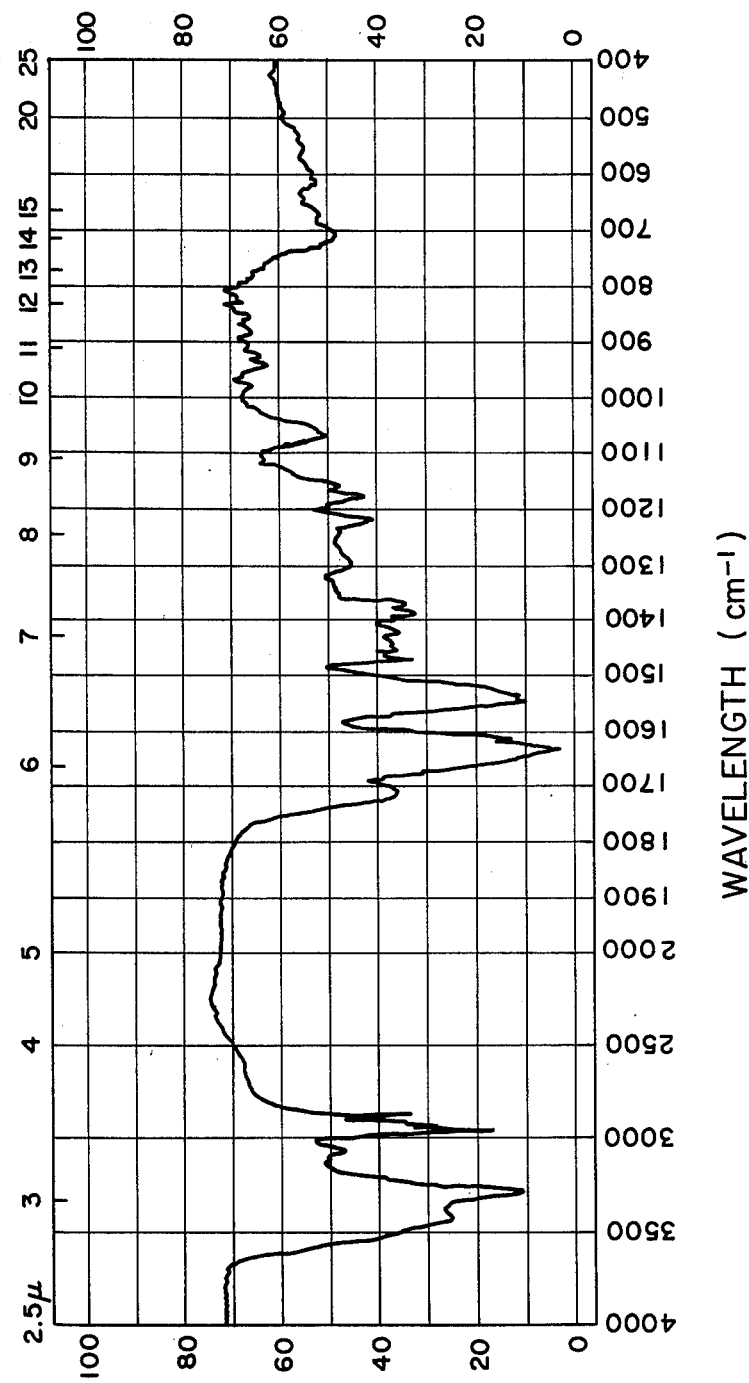
Figure 8:
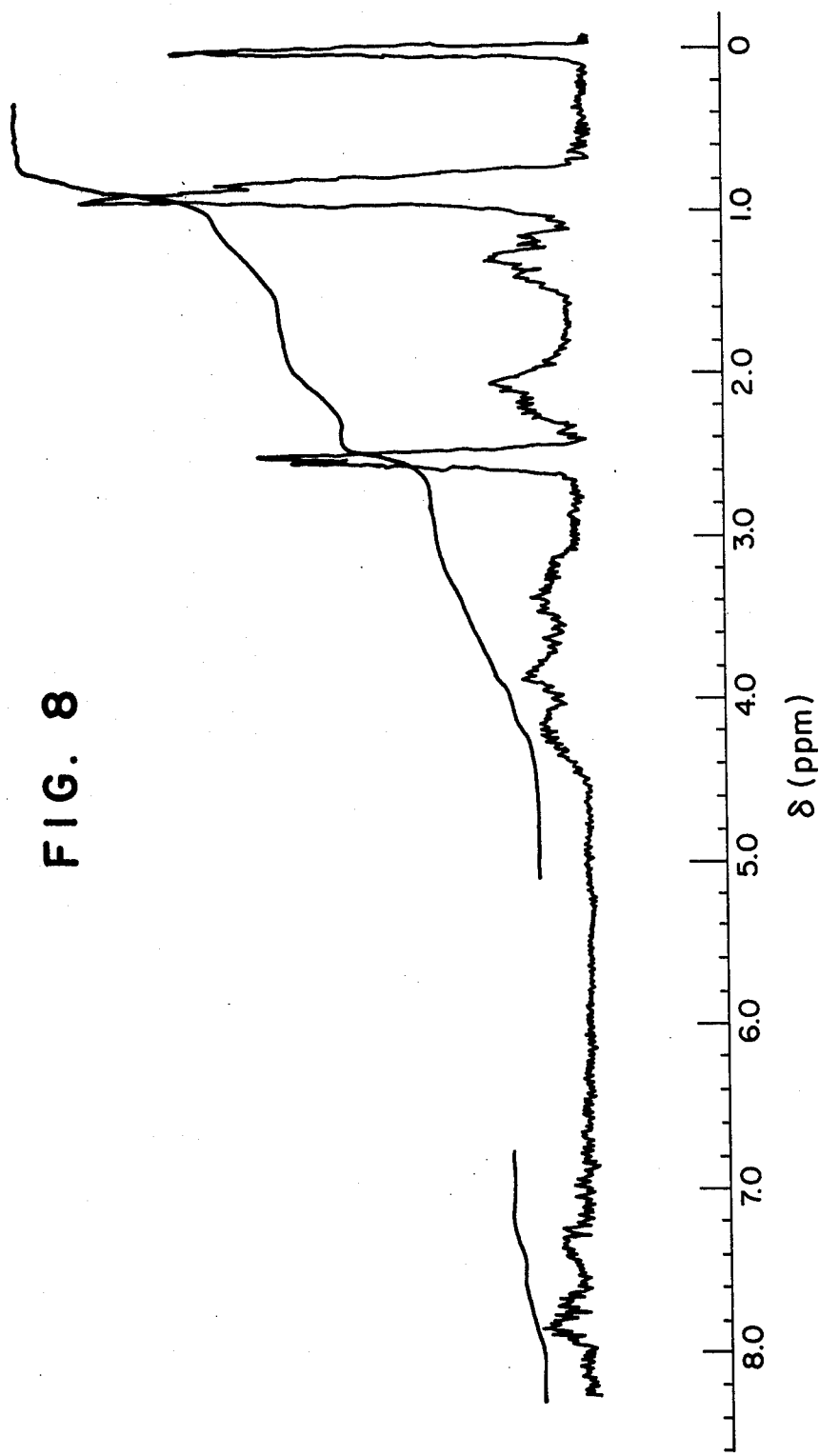
Figure 9:
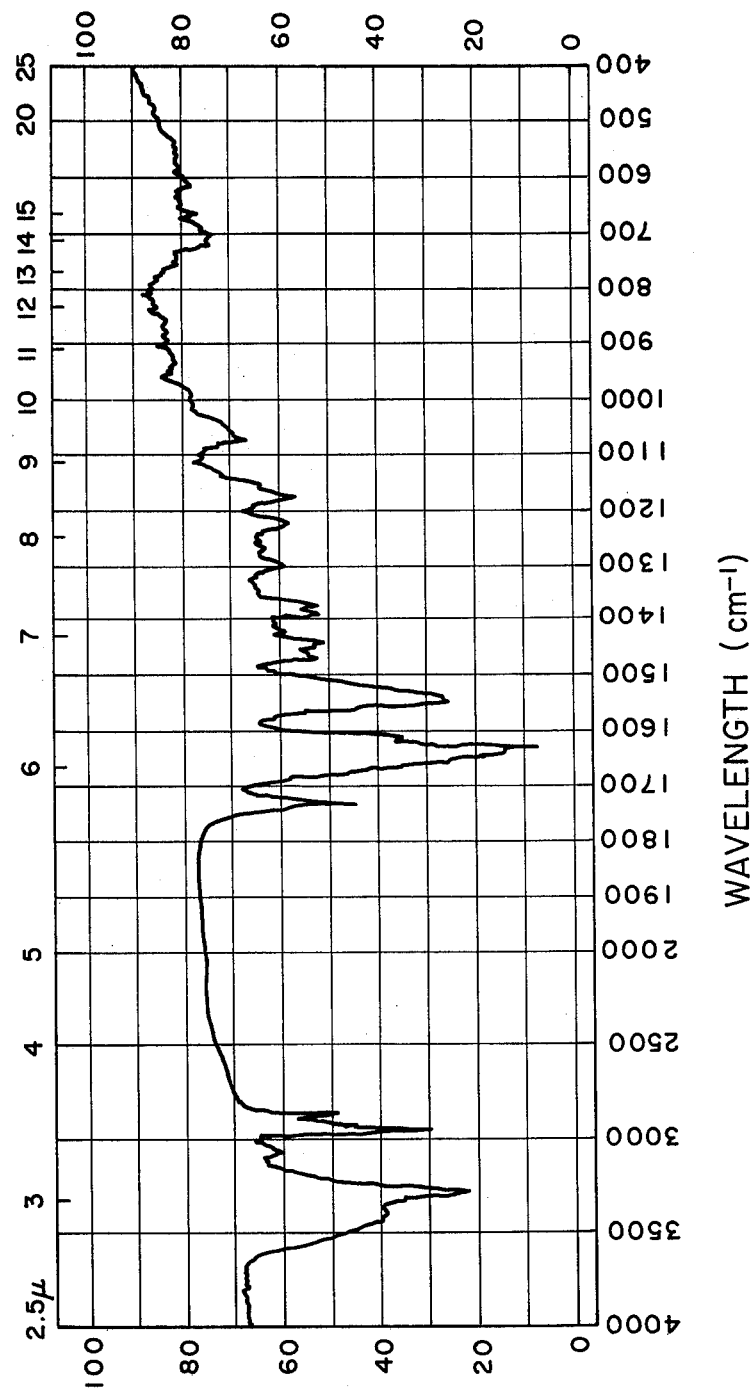
Figure 10:
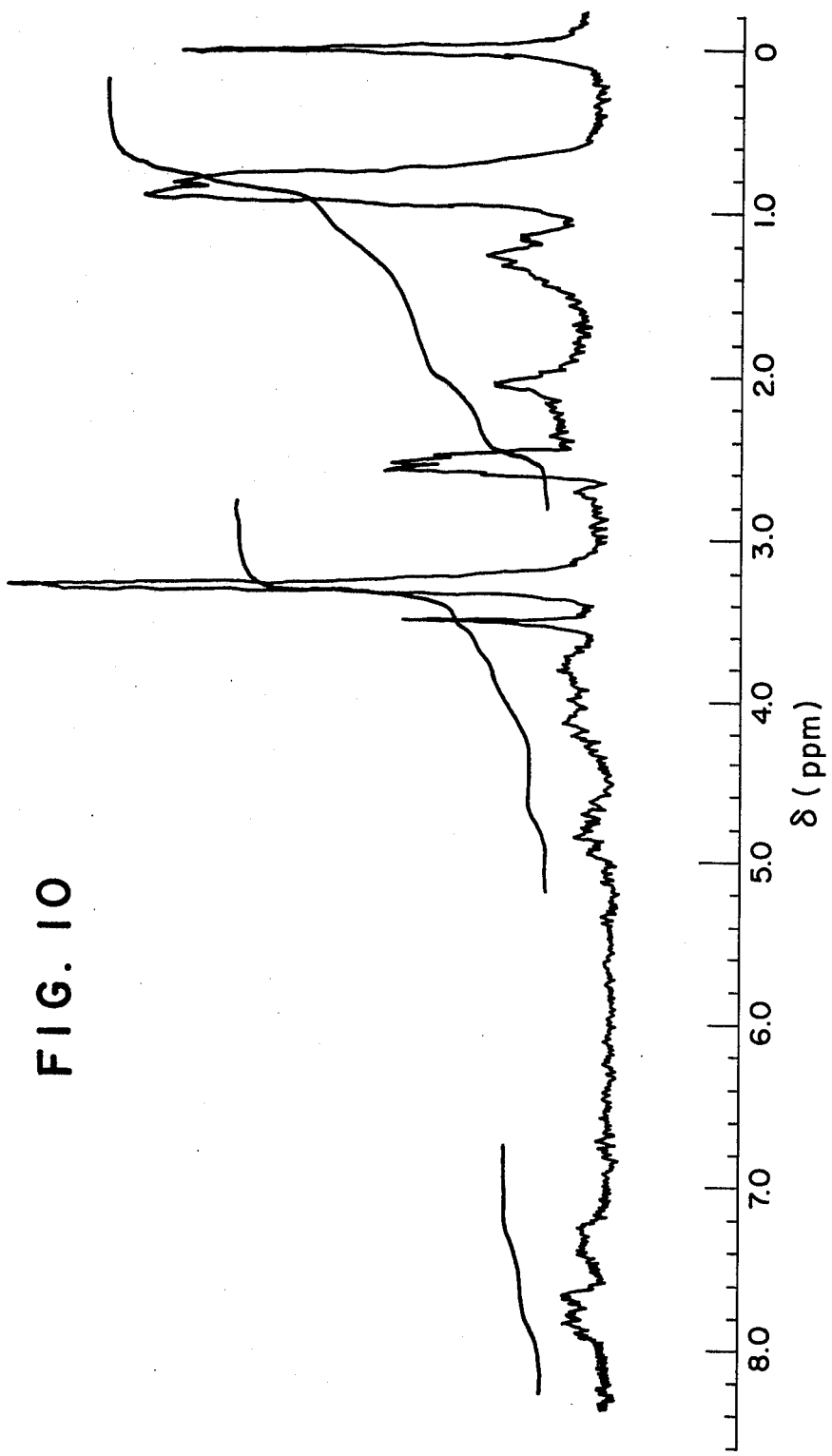

In the accompanying drawings, FIGS. 1, 3, 5, 7 and 9 show IR spectra of the procidins S-735, S-114, S-346, S-735-A and S-735-M, respectively; and FIGS. 2, 4, 6, 8 and 10 NMR spectra of the procidins S-735, S-114, S-346, S-735-A and S-735-M, respectively.

The culture medium to be used in the present invention may either be liquid or solid. Usually, however, by use of a liquid medium, shaking cultivation or cultivation under aerobic conditions is convenient. Any medium can be used, so long as the present microorganism can grow therein to accumulate the procidin in the medium. Namely, there can be used carbon sources such as glucose, lactose, glycerin, starch, sucrose, dextrin, molasses, organic acids, etc. and nitrogen sources such as protelolysis products, e.g. peptone, casamino acid or N-Z-amine, meat extract, yeast extract, soybean grains, corn steep liquor, amino acids, ammonium salts, nitrates and other organic or inorganic nitrogen-containing compounds. Addition of L-leucine to the medium is found to be necessary for producing S-114 and S-346. The amount of L-leucine added is preferably from 0.5 to 2.0%, which is variable depending on the culture conditions. As inorganic salts, various phosphates, magnesium sulfate, sodium chloride and the like may be added. For acceleration of growth of the microorganism, vitamins or compounds related with nucleic acids can also be added. In some cases, addition of defoaming agent such as silicone, polypropylene glycol derivatives or soybean oil may also be effective in increasing the amount of procidins accumulated in the medium.

In practicing cultivation, it is desired to inoculate to the medium a seed obtained by pre-incubation previously conducted on a small scale. The cultivation conditions such as cultivation temperature and cultivation period are suitably selected and controlled so as to obtain the maximum amount of procidins to be accumulated. In many cases, cultivation is conducted preferably under aerobic conditions at 25° C to 35° 1 C for 2 to 7 days at pH in the range from 4 to 9.5.

In the thus cultivated product, procidins are produced and accumulated. When cultivation is carried out by use of a liquid medium, the product is accumulated principally in the liquid portion. Accordingly, the cultured product is first subjected to filtration or centrifugation to remove microorganism cells, followed by separation of the product from the filtrate or the supernatant obtained. Alternatively, the product can directly be separated from the cultured product without removal of the microorganism cells. Separation and purification of the desired product from the cultured product can easily be effected by various combination of methods based on the chemical properties of procidins. For example, precipitation by addition of a precipitating agent such as ammonium sulfate; extraction with an organic solvent such as n-butanol which is not freely miscible with water but can dissolve procidins; dissolution into a polar solvent such as methanol or ethanol; removal of impurities by treatment with hexane, etc.; gel filtration with Sephadex (Pharmacia Fine Chemicals) ion-exchange chromatography with various ion-exchangers such as ion-exchange resins, ion-exchange cellulose, ion-exchange Sephadex (Pharmacia Fine Chemicals), etc.; and adsorption chromatography with adsorbents such as activated charcoal, alumina, silica gel, Amberlite XAD-1,2, etc. can effectively be utilized. Additionally, other purification methods based on the properties of procidins can of course suitably be available. By suitable combination of these methods, procidins can be isolated from the cultured product in the form of crystals.

Table 1 shows $R_f$ values of S-735, S-114, S-346, S-735-A and S-735-M measured by thin-layer chromatography in various solvent systems. Silica gel thin-layer produced by Merck Co. (trade number 5715, layer thickness 0.25 mm) is used as the thin-layer and development is carried out at room temperature.

Table 1

| Procidins | $R_f$ values | | |
|---|---|---|---|
| | Solvent system A | Solvent system B | Solvent system C |
| S-735 | 0.30 | 0.84 | 0.61 |
| S-114 | 0.15 | 0.58 | 0.57 |
| S-346 | 0.16 | 0.62 | 0.63 |
| S-735-A | 0.14 | 0.54 | 0.49 |
| S-735-M | 0.42 | 0.88 | 0.65 |

Notes)
Solvent system A: chloroform-methanol-acetic acid (92.5 : 6 : 1.2)
Solvent system B: chloroform-methanol-acetic acid (86 : 12 : 2)
Solvent system C: butanol-butyl acetate-acetic acid-water (10 : 20 : 1 : 1)

Measurement of the pepsin inhibiting activity is carried out according to the following method.

To 1.9 ml of a reaction mixture comprising 1.0 ml of 0.6% casein solution wherein substrate casein (Wako Junyaku Co., Japan) is dissolved in 0.08 M lactic acid buffer solution (pH 2.2), 0.7 ml of 0.02N hydrochloric acid-0.02M potassium chloride buffer solution (pH 2.2) and 0.2 ml of a sample solution containing procidin is added 0.1 ml of crystalline pepsin (Sigma Chemical Company) solution with a concentration of 40 μg/ml. After the reaction is carried out at 37° C for 30 minutes, the reaction is terminated by addition of 2.0 ml of 1.7M perchloric acid solution. After the reaction is left to stand for additional one hour at room temperature, it is subjected to centrifugation, followed by measurement of the absorbance (A) of resulting supernatant at 280 mμ. On the other hand, reference sample by use of only the buffer solution containing no procidin is subjected in the same manner to measurement of absorbance (B).

The inhibiting degree is calculated from $(B - A)/B \times 100$. The amount of procidin necessary for inhibiting 50% activity of 4 μg crystalline pepsin ($ID_{50}$), when measured according to this method, is given in the following Table 2:

Table 2

|  | S-735 | S-114 | S-346 |
|---|---|---|---|
| Amount necessary for inhibiting 50% pepsin (4 μg) ($ID_{50}$) | 0.02 μg | 0.02 μg | 0.02 μg |

To explain in detail about the anti-ulcer action of the typical procidin of the present invention, namely S-735, the effect of S-735 against the gastric ulcer caused by ligature of the pylorus (Shay. rat) is as shown in Table 3.

Table 3

| Anti-ulcer action of S-735 | | | | |
|---|---|---|---|---|
| Dosage (mg/kg) | Animal numbers | Amount of secretion of gastric juice (ml) | Pepsin activity (μg/ml) | Average ulcer score |
| 0 | 6 | 3.10 ± 0.18 | 6.23 ± 0.37 | 6 |
| 0.5 | 4 | 4.50 ± 0.34 | 0.51 ± 0.32 | 3.75 |
| 5.0 | 4 | 5.08 ± 0.27 | 0 | 0 |

Notes)
1. Rat: Wister type HLA male, body weight from 180 to 240 g.
2. Immediately after ligature of pylorus, S-735 is orally administered. After 18 hours, stomach is extracted to observe whether there is ulcer with naked eyes. The degree of ulcer is rated at six ranks with scores of 0 to 6.

Toxicity of S-735 is extremely low and $LD_{50}$ value for mouse is 5 g/Kg or more by oral administration and 0.5 g/Kg or more by interabdominal injection. Thus, the procidins of the present invention are very low in toxicity and yet have very strong pepsin inhibiting activity. Therefore, they are useful as medicines for preventing or healing gastric and duodenal ulcers for which pepsin is considered to be one of the causes.

The present invention is described in further detail by referring to the following examples, which are set forth for not limiting but illustrative purpose only.

EXAMPLE 1

*Streptomyces procidinanus* was inoculated in a Sakaguchi's flask of 500 ml capacity containing 100 ml of a sterilized liquid medium of pH 7.0 having the following composition:

| Glucose | 1.0% |
|---|---|
| Lactose | 1.0% |
| Soybean powder | 1.0% |
| Meat extract | 0.5% |
| Peptone | 0.5% |
| Sodium chloride | 0.3% |
| Magnesium sulfate | 0.1% |
| Dipotassium phosphate | 0.1% |

Cultivation was carried out at 28° C for two days under reciprocal shaking. The culture broth was apportioned each in 2.0 ml into 30 Sakaguchi's flasks of 500 ml capacity each containing 100 ml of the above sterilized liquid medium and cultivation was continued in each flask at 28° C for 7 days under reciprocal shaking to obtain 3.0 liters of culture broth. Said culture broth was filtrated and the resulting filtrate was treated twice with 2.0 liters of n-butanol to extract active substances. The extract with n-butanol was concentrated and the concentrate obtained was admixed with 200 ml of methanol to be dissolved therein. The solution was then passed through a column of 100 ml of activated charcoal. 500 Milliliters of eluate were collected and concentrated to obtain 1.8 g of pale yellow powders. The powders, after being dissolved in methanol and coated on 2 g of silica gel, were superposed on 150 g of silica gel, which were packed in a column (diameter:2.6 cm) and equilibrated with a mixed solvent comprising chloroform, methanol and acetic acid (92.5:6:1.2), and then eluted with said mixed solvent. The eluate obtained in fractions of each 15 g was analyzed by thin-layer chromatography. As the result, S-735-M was found to be eluted in fraction Nos. 43 to 51, S-735 in fraction Nos. 53 to 67, and S-735-A in fraction Nos. 72 to 85. The respective fractions were collected, concentrated and dried, followed by recrystallization from anhydrous methanol repeated twice, whereby 20 mg of S-735-M, 18 mg of S-735 and 180 mg of S-735-A were obtained as fine needles, respectively.

EXAMPLE 2

The strain Streptomyces procidinanus was inoculated in four Sakaguchi's flasks of 500 ml capacity each containing 100 ml of a sterilized liquid medium of pH 7.0 having the following composition:

| Glucose | 2.0% |
|---|---|
| Lactose | 1.0% |
| Soybean powder | 1.0% |
| Meat extract | 0.75% |
| Peptone | 0.75% |
| Sodium chloride | 0.3% |
| Magnesium sulfate | 0.1% |
| Dipotassium phosphate | 0.1% |

Cultivation was carried out at 28° C for two days under reciprocal shaking to obtain 400 ml of a culture broth. The culture broth was transferred into two tanks of 25 liter capacity each containing 12 liter of the above sterilized liquid medium. While adding about 100 ml of silicone into each tank, cultivation was carried out at 28° C for 72 hours under aerating stirring. The culture broth was filtrated and the resulting filtrate was treated twice with about 15 liter of n-butanol to extract active substances. The extract with n-butanol was concentrated. After the concentrate was washed with one liter of hexane, 500 ml of methanol was added to dissolve the concentrate. The solution was passed through a column of 300 ml activated charcoal to collect 1.5 liter of eluate. The eluate was concentrated to obtain 5.6 g of yellowish brown powders. The powders, after being dissolved in methanol and coated on 3 g of silica gel, were superposed on 200 g of silica gel, which were packed in a column (diameter:4.5 cm) and equilibrated with a mixture solvent comprising chloroform, methanol and acetic acid (92.5:6:1.2), and eluted with said mixed solvent. When the eluate was collected in fractions of each 15 g, S-735-M was found to be eluted in fraction Nos. 93 to 101, S-735 in fraction Nos. 109 to 121 and S-735-A in fraction Nos. 125 to 134. The respective fractions were collected, concentrated and dried, followed by recrystallization from anhydrous methanol repeated twice, whereby 140 mg of S-735-M, 160 mg of S-735 and 1680 mg of S-735-A were obtained, respectively, as white needles.

EXAMPLE 3

(1) The strain *Streptomyces procidinanus* was inoculated in a Sakaguchi's flask of 500 ml capacity containing 100 ml of a sterilized liquid medium of pH 7.0 having the following composition:

| | |
|---|---|
| Glucose | 1.0% |
| Lactose | 1.0% |
| Soybean powder | 1.0% |
| Meat extract | 0.5% |
| Peptone | 0.5% |
| Sodium chloride | 0.3% |
| Magnesium sulfate | 0.1% |
| Dipotassium phosphate | 0.1% |

Shaking cultivation was carried out at 28° C for two days. The culture broth was further apportioned each in 10 ml into 10 Sakaguchi's flasks of 2 liter capacity each containing 500 ml of a sterilized liquid medium of pH 7.0 having the following composition:

| | |
|---|---|
| Glucose | 1.0% |
| Lactose | 1.0% |
| Soybean powder | 1.0% |
| L-leucine | 1.0% |
| Meat extract | 0.5% |
| Peptone | 0.5% |
| Sodium chloride | 0.3% |
| Magnesium sulfate | 0.1% |
| Dipotassium phosphate | 0.1% |

In each flask, cultivation was carried out at 28° C for 7 days under reciprocal shaking to obtain 5.0 liter of the culture broth. The culture broth was filtrated and the resulting filtrate was passed through a column of 3.3 cm in diameter in which 120 g of activated charcoal for chromatography (Wako Junyaku Co., Japan) wetted with water (480 ml) was packed. After the column was washed with 6.0 liter of water and 3.0 liter of 40% methanol, warmed elution with 3.0 liter of methanol was effected at 40° C. The eluate eluted with methanol was concentrated under reduced pressure to obtain 4.1 g of pale yellow crude powders. The crude powders were dissolved in methanol and passed through a column of 2.2 cm in diameter in which 40 g of activated charcoal for chromatography wetted with methanol was packed. The eluate eluted with 300 ml of methanol was concentrated under reduced pressure to obtain 2.3 g of white powders.

(2) The thus obtained white powders, after being dissolved in methanol and coated on 3.0 g of silica gel, were superposed on 200 g of silica gel, which were packed in a column (diameter:2.6 cm) and equilibrated with a mixed solvent comprising chloroform, methanol and acetic acid (86:12:2), and eluted with said mixed solvent. The eluate obtained in fractions of each 20 g was analyzed by thin-layer chromatography. As the result, S-114 and S-346 were found to be eluted in fraction Nos. 64 to 68. Said fractions were collected and concentrated under reduced pressure to obtain 1.4 g of white powders. The powders, after being dissolved in methanol and coated on 2.0 g of silica gel, were superposed on 200 g of silica gel, which were packed in a column (diameter:2.6 cm) and equilibrated with a mixed solvent comprising butanol, butyl acetate, acetic acid and water (10:20:1:1), and eluted with said mixed solvent. The eluate obtained in fractions of each 15 g was analyzed by thin-layer chromatography. As the result, S-346 was found to be eluted in fraction Nos. 64 to 70 and S-114 in fraction Nos. 73 to 85. The respective fractions were collected, concentrated and dried. After the dried products were dissolved in methanol, the solutions were left to stand in a cooled place, whereby 178 mg of S-346 and 303 mg of S-114 were obtained, respectively, as needles.

Chemical and physical properties of various procidins obtained according to the process of this invention were measured to obtain the results as listed in Table 4.

Table 4

| | S-735 | S-114 | S-346 | S-735-A | S-735-M |
|---|---|---|---|---|---|
| Elemental analysis: | C, 61.20%; H, 9.68%; N, 10.84% | C, 60.05%; H, 9.30%; N, 10.02% | C, 60.57%; H, 9.40%; N, 9.82% | C, 59.28%; H, 9.17%; N, 10.16% | C, 60.01%; H, 9.28%; N, 10.00% |
| Molecular weight: | 641 | 699 | 713 | 685 | 699 |
| Melting point: | 253–255° C | 231–233° C | 214–216° C | 233–235° C | 269–271° C |
| Specific rotatory power$[\alpha]_D^{25}$ | −83.45 (0.145%, methanol) | −78.61 (0.533%, methanol) | −71.95 (0.492%, methanol) | −86.86 (0.152%, methanol) | −85.42 (1.828%, methanol) |
| UV absorption spectrum: | No maximum absorption at 210 mμ–400 mμ | No maximum absorption at 210 mμ–400 mμ | No maximum absorption at 210 mμ–400 mμ | No maximum absorption at 210 mμ–400 mμ | No maximum absorption at 210 mμ–400 mμ |
| IR absorption spectrum: | FIG. 1 | FIG. 3 | FIG. 5 | FIG. 7 | FIG. 9 |
| NMR spectrum: | FIG. 2 | FIG. 4 | FIG. 6 | FIG. 8 | FIG. 10 |
| Mass spectrum: | Molecular ion peak: 641 m/e | Molecular ion peak of methyl ester: 713 m/e | Molecular ion peak of methyl ester: 727 m/e | Molecular ion peak of methyl ester: 699 m/e | Molecular ion peak: 699 m/e |
| Constituents: | Alanine: Valine: 4-amino-3-hydroxy-6-methyl heptanoic acid: 3-amino-2-hydroxy-5-methyl hexane: iso-valeric acid= 1:2:1:1:1 | Alanine: Valine: Leucine: 4-amino-3-hydroxy-6-methyl-heptanoic acid: iso-valeric acid= 1:1:1:2:1 | Alanine: Leucine: 4-amino-3-hydroxy-6-methyl-heptanoic acid: iso-valeric acid= 1:2:2:1 | Alanine: Valine: 4-amino-3-hydroxy-6-methyl-heptanoic acid: iso-valeric acid= 1:2:2:1 | Alanine: Valine: 4-amino-3-hydroxy-6-methyl-heptanoic acid: 4-amino-3-hydroxy-6-methyl-heptanoic acid methyl ester: iso-valeric acid: 1:2:1:1:1 |

What is claimed is:
1. A procidin of the general formula:

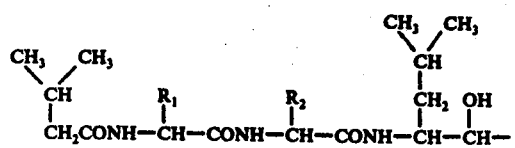

wherein $R_1$ and $R_2$, which may either be identical or different, represent isopropyl or isopropyl methyl; and $R_3$ represents hydrogen when both $R_1$ and $R_2$ are isopropyl or carboxylic when $R_1$ and $R_2$ are different or both $R_1$ and $R_2$ are isopropyl methyl, said procidin occurring as a mixture of compounds when $R_1$ and $R_2$ are different.

2. The procidin according to claim 1, which has the following formula:

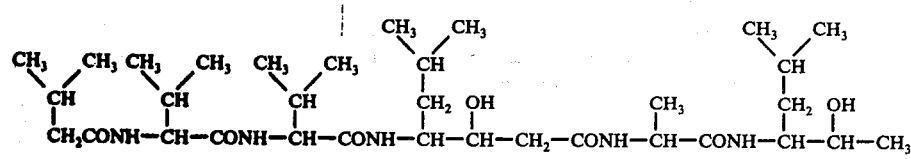

3. The procidin according to claim 1, which has the following formula:

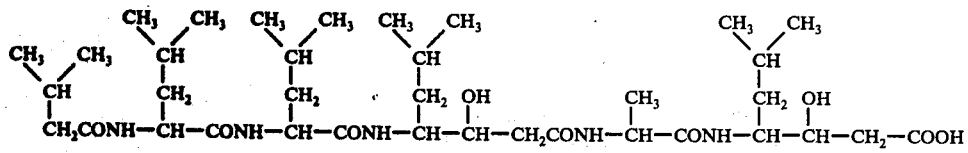

4. The procidin according to claim 1, which is a mixture of compounds having the following formulas:

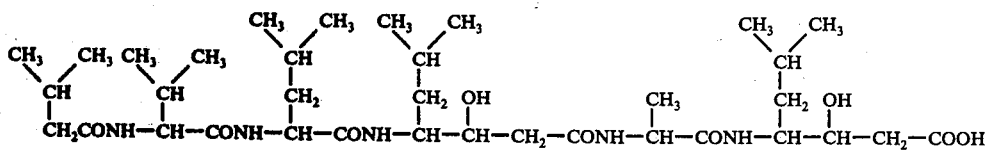

and

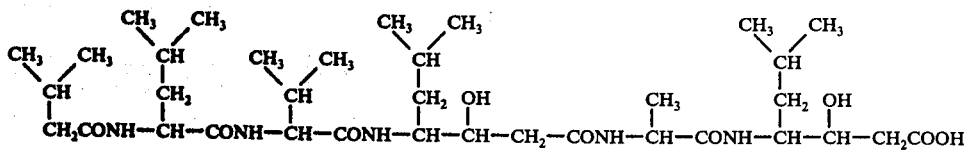

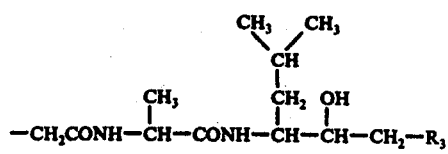

5. A pharmaceutical composition comprising a procidin of claim 1 and a pharmaceutically acceptable carrier.

6. A method of healing or preventing ulcer formation comprising administering a procidin of claim 1 in an amount effective to heal or prevent ulcer formation.

* * * * *

UNITED STATES PATENT AND TRADEMARK OFFICE
CERTIFICATE OF CORRECTION

PATENT NO. : 4,091,093  Page 1 of 2
DATED : May 23, 1978
INVENTOR(S) : S. Kojima et al It is certified that error appears in the above—identified patent and that said Letters Patent is hereby corrected as shown below:

In the Abstract, line 3, delete "*Streptomyces procidinanus*" and insert --*Actinomadura sp.*--

Col. 1, line 7, delete "Streptomyces" and insert --Actinomadura--
Col. 1, line 13, delete "Streptomyces" and insert --Actinomadura--
Col. 1, line 23, delete "*Streptomyces procidinanus*" and insert --*Actinomadura sp.*--
Col. 2, line 49, delete "Streptomyces" and insert --Actinomadura--
Col. 4, line 2, delete "*Streptomyces procidinanus*" and insert --*Actinomadura sp.*--
Col. 4, line 4, delete "*Streptomyces procidinanus*" and insert --*Actinomadura sp.*--
Col. 5, line 18, delete "*Streptomyces procidinanus*" and insert --*Actinomadura sp.*--
Col. 7, line 41, delete "*Streptomyces procidinanus*" and insert --*Actinomadura sp.*--

UNITED STATES PATENT AND TRADEMARK OFFICE
CERTIFICATE OF CORRECTION

PATENT NO. : 4,091,093

DATED : May 23, 1978

INVENTOR(S) : S. Kojima et al

It is certified that error appears in the above—identified patent and that said Letters Patent is hereby corrected as shown below:

Col. 8, line 18, delete "*Streptomyces procidinanus*" and insert --*Actinomadura sp.*--

Col. 8, line 65, delete "*Streptomyces procidinanus*" and insert --*Actinomadura sp.*--

Signed and Sealed this

First Day of November 1983

[SEAL]

*Attest:*

*Attesting Officer*

GERALD J. MOSSINGHOFF

*Commissioner of Patents and Trademarks*